United States Patent
Vale et al.

(10) Patent No.: US 12,133,657 B2
(45) Date of Patent: Nov. 5, 2024

(54) CLOT RETRIEVAL DEVICE FOR REMOVING OCCLUSIVE CLOT FROM A BLOOD VESSEL

(71) Applicant: NEURAVI LIMITED, Galway (IE)

(72) Inventors: David Vale, Barna (IE); Brendan Casey, Barna (IE); Brian Fahy, Galway (IE); Eamon Brady, Loughrea (IE); Maeve Holian, Galway (IE); Daniel King, Galway (IE); Michael Gilvarry, Galway (IE); Jacqueline O'Gorman, Clare (IE)

(73) Assignee: NEURAVI LIMITED, Galway (IE)

( * ) Notice: Subject to any disclaimer, the term of this patent is extended or adjusted under 35 U.S.C. 154(b) by 471 days.

(21) Appl. No.: 17/476,573

(22) Filed: Sep. 16, 2021

(65) Prior Publication Data

US 2022/0000504 A1 Jan. 6, 2022

Related U.S. Application Data

(63) Continuation of application No. 16/330,703, filed as application No. PCT/EP2017/072030 on Sep. 1, 2017, now Pat. No. 11,147,572.
(Continued)

(51) Int. Cl.
*A61B 17/221* (2006.01)
*A61B 17/00* (2006.01)
(Continued)

(52) U.S. Cl.
CPC .... *A61B 17/221* (2013.01); *A61B 17/320725* (2013.01); *A61B 2017/00867* (2013.01);
(Continued)

(58) Field of Classification Search
CPC ............ A61B 17/221; A61B 17/22031; A61B 17/320725; A61B 2017/2212;
(Continued)

(56) References Cited

U.S. PATENT DOCUMENTS

| 4,455,717 A | 6/1984 | Gray |
| 4,611,594 A | 9/1986 | Grayhack et al. |

(Continued)

FOREIGN PATENT DOCUMENTS

| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)

*Primary Examiner* — Kankindi Rwego
(74) *Attorney, Agent, or Firm* — Troutman Pepper Hamilton Sanders LLP

(57) ABSTRACT

A clot retrieval device for removing occlusive clot from a blood vessel. The device comprises an inner elongate body having a collapsed delivery configuration and an expanded deployed configuration. An outer elongate body is at least partially overlying the inner elongate body. The outer elongate body is expandable to a radial extent which is greater than the radial extent of the inner body in the deployed configuration to define a clot reception space. The outer elongate body has a plurality of clot receiving openings and a plurality of clot engaging regions. The clot engaging regions are adapted, on engagement with clot, to urge clot towards the clot receiving openings and into the reception space between the outer elongate body and the inner elongate body, wherein the radial force profile of the device varies along the length of the device.

20 Claims, 6 Drawing Sheets

Related U.S. Application Data

(60) Provisional application No. 62/383,905, filed on Sep. 6, 2016.

(51) Int. Cl.
*A61B 17/22* (2006.01)
*A61B 17/3207* (2006.01)
*A61B 90/00* (2016.01)

(52) U.S. Cl.
CPC .............. *A61B 2017/22079* (2013.01); *A61B 2090/3966* (2016.02)

(58) Field of Classification Search
CPC .... A61B 2017/2215; A61B 2017/2217; A61B 2017/22034; A61B 2017/22035; A61B 2090/3966
USPC ........................................................ 606/200
See application file for complete search history.

(56) References Cited

U.S. PATENT DOCUMENTS

| | | |
|---|---|---|
| 4,612,931 A | 9/1986 | Dormia |
| 4,643,184 A | 2/1987 | Mobin-Uddin |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | MacGregor et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,733,325 A | 3/1998 | Robinson et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,824,041 A | 10/1998 | Lenker et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,174,329 B1 | 1/2001 | Callol et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |

(56) References Cited

U.S. PATENT DOCUMENTS

| | | |
|---|---|---|
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Andau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |

(56) References Cited

U.S. PATENT DOCUMENTS

| | | |
|---|---|---|
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,147,572 B2 * | 10/2021 | Vale ............... A61B 17/221 |
| 11,439,418 B2 | 9/2022 | O'Malley |
| 11,517,340 B2 | 12/2022 | Casey |
| 2001/0001315 A1 | 5/2001 | Bates et al. |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |

(56) References Cited

U.S. PATENT DOCUMENTS

| | | |
|---|---|---|
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zadno-Azizi et al. |
| 2002/0095171 A1 | 7/2002 | Belef |
| 2002/0123765 A1 | 9/2002 | Sepetka et al. |
| 2002/0128680 A1 | 9/2002 | Pavolvic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0069520 A1 | 4/2003 | Skujins et al. |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0010245 A1 | 1/2005 | Wasicek |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0171566 A1 | 8/2005 | Kanamaru |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0135826 A1 | 6/2007 | Zaver et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |

(56) References Cited

U.S. PATENT DOCUMENTS

| | | |
|---|---|---|
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0296274 A1 | 12/2008 | Bialas et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0022572 A1 | 1/2012 | Braun et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |

(56) References Cited

U.S. PATENT DOCUMENTS

| | | |
|---|---|---|
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |

(56) References Cited

U.S. PATENT DOCUMENTS

| | | |
|---|---|---|
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0005321 A1 | 1/2021 | Hwang |
| 2021/0007757 A1 | 1/2021 | Casey et al. |
| 2021/0228223 A1 | 7/2021 | Casey et al. |
| 2022/0192739 A1 | 6/2022 | Deen et al. |

FOREIGN PATENT DOCUMENTS

| | | |
|---|---|---|
| CN | 102307613 A | 1/2012 |
| CN | 102316809 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3593742 A1 | 1/2020 |
| EP | 3669802 A1 | 6/2020 |
| EP | 3858291 A1 | 8/2021 |
| ES | 2210456 T3 | 7/2004 |
| GB | 2427554 A | 1/2007 |
| GB | 2494820 A | 3/2013 |
| JP | 09-19438 A | 1/1997 |
| JP | 2014-511223 A | 5/2014 |
| JP | 2014-525796 A | 10/2014 |
| JP | 2015-505250 A | 2/2015 |
| JP | 2016-513505 A | 5/2016 |
| JP | 2019-526365 A | 9/2019 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/030751 A1 | 4/2003 |
| WO | WO 03/051448 A2 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2008/135823 A1 | 11/2008 |
| WO | WO 2009/031338 A1 | 3/2009 |
| WO | WO 2009/076482 A1 | 6/2009 |
| WO | WO 2009/086482 A1 | 7/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |
| WO | WO 2016/089451 A1 | 6/2016 |
| WO | WO 2017/089424 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

\* cited by examiner

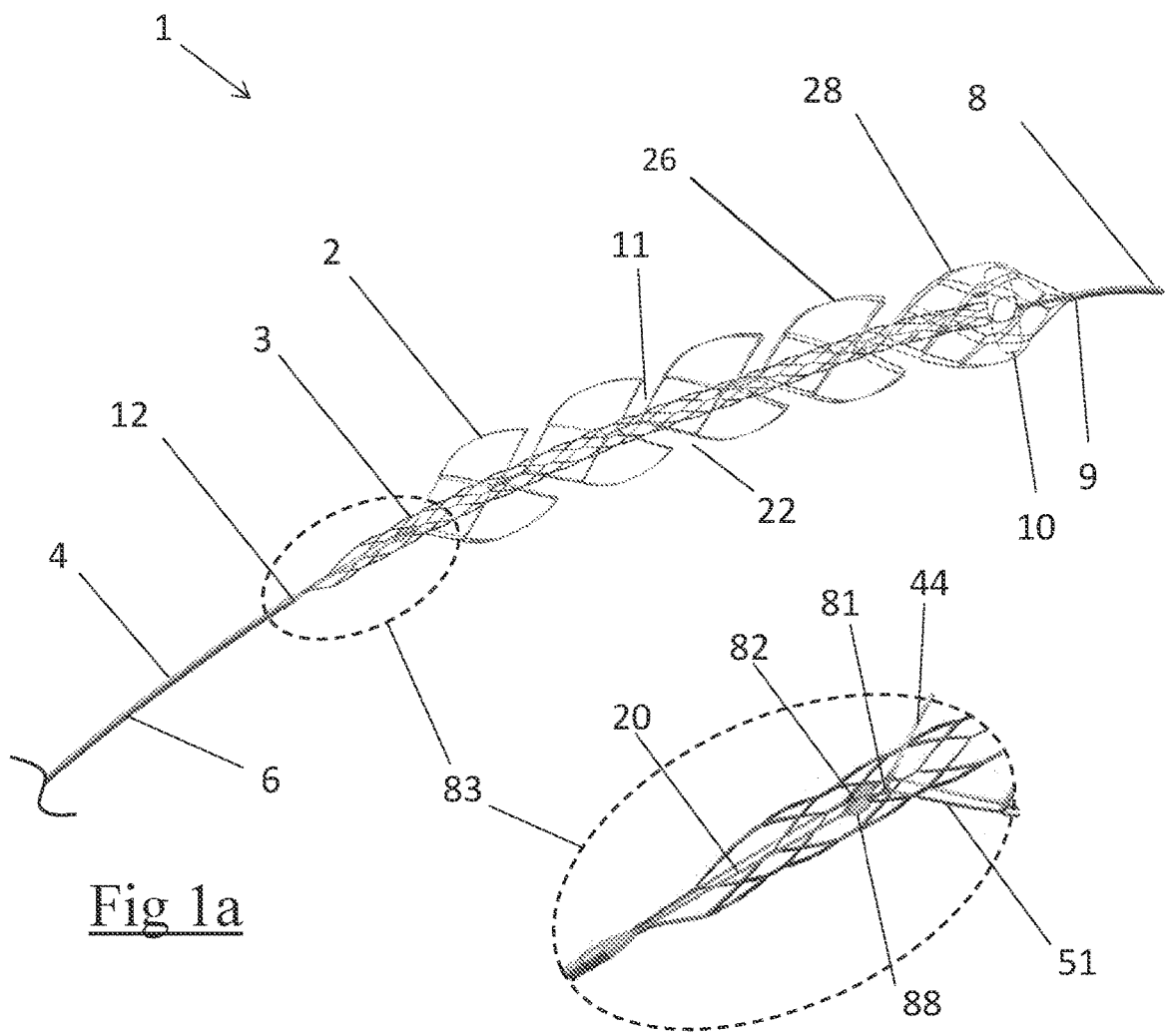
Fig 1a
Fig 1c
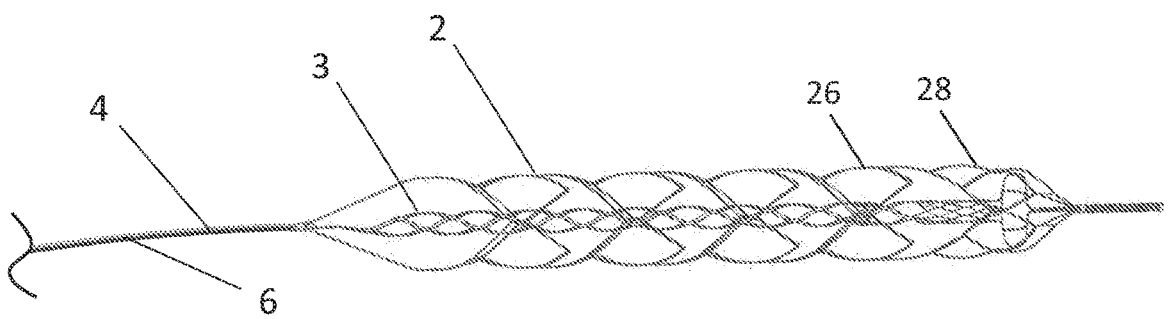
Fig 1b

CLOT RETRIEVAL DEVICE FOR REMOVING OCCLUSIVE CLOT FROM A BLOOD VESSEL

CROSS REFERENCE TO RELATED APPLICATIONS

This application is a continuation application of U.S. application Ser. No. 16/330,703, filed Mar. 5, 2019, which is a U.S. national phase application under 35 U.S.C. § 371 of International Patent Application No. PCT/EP2017/072030, filed Sep. 1, 2017, which claims benefit of priority to U.S. Provisional Patent Application No. 62/383,905, filed Sep. 6, 2016. The entire contents of these applications are hereby incorporated by reference.

FIELD OF THE INVENTION

This invention relates to devices and methods of removing acute blockages from blood vessels. The invention especially relates to removing acute obstructions from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clot from cerebral arteries in patients suffering acute ischemic stroke (AIS), from pulmonary arteries in patients suffering from pulmonary embolism (PE), from coronary native or graft vessels in patients suffering from myocardial infarction (MI), and from other peripheral arterial and venous vessels in which clot is causing an occlusion.

BACKGROUND

There are significant challenges associated with designing clot removal devices that can deliver high levels of performance:

There are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty. The tortuosity challenge is even more severe in the arteries approaching the brain. For example, it is not unusual at the distal end of the internal carotid artery that the device will have to navigate a vessel segment with a 180° bend, a 90° bend and a 360° bend in quick succession over a few centimeters of vessel. In the case of pulmonary embolisms, access may be gained through the venous system and then through the right atrium and ventricle of the heart. The right ventricular outflow tract and pulmonary arteries are delicate vessels that can easily be damaged by inflexible or high profile devices. For these reasons it is desirable that the clot retrieval device be compatible with as low profile and flexible access and support catheters as possible.

The vasculature in the area in which the clot may be lodged is often fragile and delicate. For example, neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

The clot may comprise any of a range of morphologies and consistencies. Long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore, the inventors have discovered that the properties of the clot may be significantly changed by the action of the devices interacting with it. In particular compression of blood clot causes dehydration of the clot and results in a dramatic increase in both clot stiffness and coefficient of friction.

The clots may not only range in shape and consistency, but also may vary greatly in length, even in any one given area of the anatomy. For example, clots occluding the middle cerebral artery of an ischemic stroke patient may range from just a few millimeters to several centimeters in length.

Stent-like clot retrievers are being increasingly used to remove clot from cerebral vessels of acute stroke patients. These are self expanding devices, similar in appearance to a stent attached to the end of a long shaft and are advanced through a microcatheter and deployed across clot obstructions in order to trap and retrieve them. They rely on a pinning mechanism to grab the clot by trapping the clot between the self-expanding stent-like body and the vessel wall. This approach has a number of disadvantages:

A stent-like clot retriever relies on its outward radial force (RF) to retain its grip on the clot. If the RF is too low the stent-like clot retriever will lose its grip on the clot, but if the RF is too high the stent-like clot retriever may damage the vessel wall and may require too much force to withdraw. Therefore stent-like clot retrievers that have sufficient radial force to deal with all clot types may cause vessel trauma and serious patient injury, and stent-like clot retrievers that have appropriate radial force to remain atraumatic may not be able to effectively handle all clot types.

The stent-like clot retriever pinning mechanism tends to compress the trapped clot. This compressive force will tend to dehydrate the clot, which in turn tends to increase its coefficient of friction, making it more difficult to remove from the vessel.

Conventional Stent-like clot retriever designs do not retain their expanded shape very well when placed in tension in bends, due to the manner in which their strut elements are connected to one another. This can result in a loss of grip on a clot as the stent-like clot retriever is withdrawn proximally around a bend in a tortuous vessel, with the potential escape of the captured clot. This occurs because the struts of the stent-like clot retriever are placed in tension when it is retracted. This tension is due to friction between the device and the blood vessel and is increased if an additional load is applied load such as that provided by a clot. In a bend the struts on the outside of the bend are placed in higher tension than those on the inside. In order to attain the lowest possible energy state the outside surface of the stent moves towards the inside surface of the bend, which reduces the tension in the struts, but also reduces the expanded diameter of the stent-like clot retriever.

Another disadvantage with this approach is that it relies on pinning the clot between the stent-like clot retriever and the vessel wall and thus may not restrain the clot effectively when passing a branch vessel or when passing into a vessel that is larger than the fully expanded diameter of the stent-like clot retriever.

Pinning the clot between the stent-like clot retriever and the vessel wall in order to remove it from the vessel also results in high shear forces against the side of the clot as it is removed, potentially releasing fragments of the clot. If these fragments are not retained by the device they may be released leading to further blockages in the distal vasculature.

A particular difficulty encountered when attempting to remove long clots is that conventional devices may be shorter than the clot itself. A device that is shorter than the clot is unlikely to be able to restore flow through the occluded area upon deployment, and thus the pressure gradient across the clot remains a significant impediment to its removal. Simply making such a device longer would likely render it difficult to track through tortuous anatomies and could be traumatic to the vasculature, taking more force to withdraw and potentially getting stuck and requiring surgery to remove.

For many reasons including some or all of the above limitations it is often necessary for a physician to make multiple passes with a clot retrieval device in order to fully remove an obstructive clot. However each time a clot retrieval device is withdrawn the access to the target site is lost. Thus it is necessary to re-advance a guidewire and microcatheter to access and re-cross the clot, and then remove the guidewire and advance the clot retrieval device through the microcatheter. Navigating the guidewire and microcatheter to the clot can take a considerable amount of time especially if the vessels are tortuous. This additional time and device manipulation all adds to the risks to which the patient is exposed.

The challenges described above need to be overcome for any device to provide a high level of success in removing clot, restoring flow and facilitating good patient outcomes. Existing devices do not adequately address these challenges.

STATEMENTS OF THE INVENTION

According to the invention there is provided a clot retrieval device for removing occlusive clot from a blood vessel, the device comprising:
an inner elongate body having a collapsed delivery configuration and an expanded deployed configuration;
an outer elongate body at least partially overlying the inner elongate body;
the outer elongate body being expandable to a radial extent which is greater than the radial extent of the inner body in the deployed configuration to define a clot reception space; wherein the radial force profile of the device varies along the length of the device.

In one embodiment the outer elongate body comprises a plurality of clot receiving openings and a plurality of clot engaging regions. The clot engaging may be adapted, on engagement with clot, to urge clot towards the clot receiving openings and into the reception space between the outer elongate body and the inner elongate body, In one case the radial force at a distal end of the device is lower than that at a middle section of the device.

The radial force at a distal end of the device may be lower than that of a middle section and a proximal section of the device.

In one embodiment the device comprises a plurality of segments and the radial force of one segment is different than the radial force of at least one other segment. The difference in radial force between the segments may be less than 20%, or less than 10%.

In one case the radial force increases along the length of the device from proximal to distal.

In another case the radial force of a mid segment is greater than the radial force of the distal segment.

In yet another case the radial force of a mid segment is greater than that of the proximal segment and the distal segment.

In one embodiment the outer body comprises a plurality of segments.

In one case a segment comprises a proximal ring of closed cells having a first radial force to which are connected at least one floating cell or leaflet having a second radial force which is less than the first radial force. The second radial force may be from 20% to 80%, or from 40% to 60% lower than the first radial force.

In one embodiment the clot inlet openings of the segments of the outer body differ along the length of the device.

In one case clot inlet openings in a proximal region of the device are smaller than clot inlet openings in a distal region of the device.

In another case the clot inlet openings in a middle section of the device are smaller than those in a more proximal and/or a more distal region of the device.

In a further case the clot inlet openings in a middle section of the device are larger than those in a more proximal and/or a more distal region of the device.

In one embodiment there is a gradient of the size of the clot inlet openings along the length of the device.

In one case the gradient increases from proximal to distal.

In another case the gradient decreases from proximal to distal.

In some embodiments the inner elongate body is tapered. The taper of the inner elongate body may be opposite to the gradient of the clot inlet openings in the outer body.

In another aspect of the invention the outer elongate member comprises a framework formed by struts and crowns and wherein proximal radiopaque markers are located at a distal end of struts which are proximally adjacent to proximal crowns.

According to the invention there is provided a clot retrieval device for removing occlusive clot from a blood vessel, the device comprising:—
an inner elongate body having a collapsed delivery configuration and an expanded deployed configuration;
an outer elongate body at least partially overlying the inner elongate body; the outer elongate body being expandable to a radial extent which is greater than the radial extent of the inner body in the deployed configuration to define a clot reception space; wherein the outer elongate body comprises a distal end portion; and wherein the inner elongate body comprises a main body portion and a distal portion which extends in the deployed configuration towards the outer elongate body to a greater extent than the main body portion, the distal portion of the inner elongate member and the distal end portion of the outer elongate body together defining a three dimensional protective structure to substantially prevent distal egress of clot or clot fragments from the device.

In this aspect of the invention the embolization risk is reduced by providing a distal net or scaffolding zone across the vessel lumen towards the distal end of the device. This scaffolding in this case is appended to both the inner or outer member or to both members and is three dimensional in that it has depth as well as surface area. Combining the scaffolding of both inner and outer members provides a more effective filter than utilizing one member alone. In some cases, fibers or fine wires are utilized to provide added scaffolding with minimal impact on device profile or deliverability.

In one embodiment the distal portion of the inner elongate body comprises a plurality of struts which are configured in a volumetric pattern.

In one case the distal portion of the inner elongate body comprises a bulged or flared framework of struts.

In one embodiment the distal end portion of the outer elongate body comprises distal struts. In one case the distal struts of the distal end portion of the outer elongate member are configured in a generally conical shape.

In one embodiment at least some of the struts comprise an attachment point, such as an eyelet, for reception of a fiber. The protective structure may include a plurality of fibers providing a distal net.

In one embodiment the outer elongate body comprises a first monolithic structure.

In one embodiment the inner elongate body comprises a second monolithic structure.

In one case wherein the inner elongate body extends proximally of a proximal end of the outer elongate body.

In one embodiment the outer elongate body comprises a plurality of clot receiving openings and a plurality of clot engaging regions, and wherein the clot engaging regions are adapted, on engagement with clot, to urge clot towards the clot receiving openings and into the reception space between the outer elongate body and the inner elongate body.

The clot engaging regions of the outer elongate body comprises scaffolding openings, the clot receiving openings being substantially larger than the scaffolding openings.

In one embodiment the outer elongate body comprises at least two longitudinally spaced-apart segments. There may be at least one hinge is provided between the segments.

The disclosed designs overcome many of the disadvantages of existing mechanical thrombectomy solutions.

Various interchangeable terms are used herein to describe those portions of the invention that are configured to engage with the clot, being generally deployed within the clot and engaging with it. These terms include "clot engaging portion", "expandable member", "expandable body", "clot engaging element"; while the terms "elongate basket", "engaging basket" and "stent basket" may also be used to describe this portion of the device.

Designs are disclosed in which a clot engaging portion of the device is configured to be expanded within an occlusive clot in a blood vessel so that the expanding engager allows the clot to migrate into a reception space within the body of the engager as the engager expands. The engager is delivered through a catheter to the site of the occlusion and is positioned within the clot. The engager is expandable at the site of the occlusion and starts to compress the clot as it is expanded. The engager surface comprises inlet openings and the inlet openings allow the clot to 'escape' from compression by displacing a significant portion of the clot through the inlet openings in the wall of the engager. Because a significant portion of the clot is urged through the inlet openings in the engager this minimizes compression of the clot and hence minimizes the resultant increase in the clot coefficient of friction. This also reduces the radial force on the vessel in the region of the clot which means a lesser force is required to withdraw the captured clot, which in turn means less vessel trauma and less tension on the distal vascular bed. The device is configured such that the radial force of the device acts strongly at a small diameter to engage with and grip clot but acts softly at a larger diameter to gently contact the vessel wall are also disclosed.

The radial force profile of the device may be further tailored along the device length. For example, in one embodiment of the device of this invention the radial force of the distal end of the device is lower than that of the middle section of the device. In one embodiment the radial force of the distal end of the device is lower than that of the middle and proximal sections of the device. In one embodiment of the device of this invention the device comprises a plurality of segments, and the radial force of any segment may be the same or different from the adjacent segment. In one embodiment of such a device the radial force of all the segments is balanced such that the radial force of any given segment differs by less than 20%, and more preferably by less than 10%, from the radial force of any other segment. In one embodiment of such a device the radial force of any given segment differs by less than 20%, and more preferably by less than 10%, from the radial force of an adjacent segment. In one embodiment of such a device the radial force of all the segments is tailored such that the radial force generally decreases along the length of the device from proximal to distal. In one embodiment of such a device the radial force of all the segments is tailored such that the radial force generally increases along the length of the device from proximal to distal. In another embodiment the radial force of a mid segment is greater than that of the distal segment. In another embodiment the radial force of a mid segment is greater than that of the proximal and distal segments.

The radial force of the device of this invention can be further tailored within each individual segment of the outer expandable member. In particular, a segment of the outer expandable member may comprise a proximal ring of connected closed cells of a first radial force to which are connected one or more floating cells or leaflets of a second radial force. These floating cells or leaflets are distinguished by the fact that their distal apices are not connected to a more distal portion of the device—rather they are floating or disconnected. This allows these leaflets to act as trapdoors through which clot may fall into the inner reception space of the device. They may further act as trap features which are better able to remain open and apposed to the vessel wall as the device is retracted around bends and past branch vessels, helping to retain any trapped clot. In one embodiment the second radial force is lower than the first radial force. In one embodiment the second radial force is between 20% and 80% lower than the first radial force. In a preferred embodiment the second radial force is between 40% and 60% lower than the first radial force.

Designs with dual expandable members are disclosed whereby the device comprises a first inner expandable member and a second outer expandable member the inner member being arranged substantially within the lumen of the outer member. The properties of the inner and outer members may be tailored independently of each other. The inner member may have a very different radial force to the outer member. The inner member may have a very different level of porosity to the outer member. The inner member may have a fully expanded diameter that is very different to that of the outer member. The length of the inner member may be different to that of the outer member. The shape of the struts of the inner member may be different to the shape of the struts of the outer member. There may be a clearance between the inner member and the outer member in the expanded configuration. There may be a clearance between the inner member and the outer member in the collapsed configuration. One, or both or neither of the inner and outer members may have a seam which runs substantially longitudinally along at least a portion of the wall of the member. One, or both of the inner and outer members may comprise a laser cut member, a braided member, a knitted member, an extruded member, a pultruded member, One or both of the inner and outer members may be manufactured with a process involving a laser cutting step, a braiding step, a knitting step, an extrusion step, a pultrusion step, an electropolishing step, a heat treatment step. One or both of the inner and outer members may comprise a tapered section, a flared section, a closed end section or a closed mid section. One or both members may comprise a substantially tubular or cylindrical section.

One embodiment of an inner member of this invention comprises an interconnected strut framework forming a generally tubular section, where the struts of the framework define cells or openings, and said cells or openings define the porosity of the member. This tubular section may comprise different cell patterns and a variety of cell shapes. In one embodiment there are at least two cells around the circumference of any given section through the device. In a preferred embodiment there are at least three cells around the circumference of any given section through the device. Greater numbers of cells will provide a more dense and less porous structure, which will be more capable of maintaining a flow lumen through soft clot but at the cost of device flexibility and profile. The optimum number of cells depends therefore on the consistency of the material in which the device is to be deployed and on the diameter to which the member is designed to expand. Greater diameters may require greater numbers of cells to maintain an appropriate and effective level of porosity. A cell area of less than 4.0 $mm^2$ is desired in order to achieve an adequate degree of clot scaffolding. However, a cell area of less than 0.5 $mm^2$ may cause unwanted blood coagulation or thrombosis, making the device difficult to clean for reuse and potentially generating harmful clot fragments. Therefore, a cell area of between 1.0 $mm^2$ and 3.0 $mm^2$ is most preferred.

An inner expandable member expanded diameter of between 0.75 mm and 2.5 mm is likely to be most suitable for neurovascular applications of the invention. An inner expandable member expanded diameter of between 0.75 mm and 1.75 mm with a 3 or 4 cell structure is most preferred.

The diameter of the generally tubular inner member may vary along its length. In one embodiment the inner member diameter has a generally conical shape. In one embodiment the inner member diameter tapers from a smaller proximal diameter to a larger distal diameter. In one embodiment the inner member diameter tapers from a larger proximal diameter to a smaller distal diameter. In one embodiment the inner member diameter tapers from a diameter of approximately 0.75 mm-1.75 mm to a diameter of approximately 1.5 mm-4.0 mm.

These dual expandable member devices have a number of benefits. (1) The inner member can be configured to provide a strong opening force to create a lumen through the clot and restore flow immediately on deployment. This flow lumen reduces the pressure gradient across the clot, making it easier to remove the clot. (2) The diameter to which the inner member expands may be tailored so as to reduce the risk of a reperfusion injury. With this embodiment the inner member expands to a diameter that is significantly smaller than the diameter of the vessel immediately adjacent to and distal of the occlusion. This small diameter inner member creates a small flow lumen across the occlusion and restricts the initial blood flow to the affected portion of the brain. This restricted blood flow ensures that the pressure applied to blood vessels immediately after flow restoration is lower than normal and this reduces the risk of bleeding in the ischemic vascular bed. Full perfusion is subsequently restored by removing the device and the clot. (3) The inner member may be configured to expand to a lesser diameter than the outer basket and to a lesser diameter than any vessel in which it is to be deployed. This means that a strong radial force may be safely exerted on the clot to open up a flow lumen but need not be exerted on the vessel. (4) The inner member can serve to scaffold the lumen created through the clot, preventing the liberation of emboli from the clot into the resultant fast flowing bloodstream. (5) The inner member may at least partially comprise a stent and can provide a strong grip on the clot for the critical initial step of disengaging the clot from the vessel, enabling the outer basket to be configured with a low radial force. (6) The outer member may be configured to have large inlet openings so as to urge clot across the wall of the outer. The inner member on the other hand may be configured to prevent distal migration or fragmentation or embolization of clot that traverses the wall of the outer member. By configuring the outer member so as to encourage clot to traverse the wall of the outer member the device can more effectively disengage clot from the wall of the vessel while the device is also effective at preventing loss of clot material with an inner member with a shape and substructure that provides scaffolding.

The inlet openings of the outer member may be further tailored to cater for the range of clot types and sizes that may be encountered clinically. Large inlet openings are desirable for accepting clot into the inner reception space of the device for secure clot capture but may be disadvantageous when attempting to retain a secure grip on the clot as it is retracted proximally past bends and branches. In one embodiment the inlet openings may differ along the length of the device. In one embodiment the inlet openings in a proximal region of the device are larger than the inlet openings in a distal region of the device. In one embodiment the inlet openings in a proximal region of the device are smaller than the inlet openings in a distal region of the device. In one embodiment the inlet openings in a middle section of the device are smaller than those in a more proximal and/or distal region of the device. In one embodiment the inlet openings in a middle section of the device are larger than those in a more proximal and/or distal region of the device. In one embodiment a gradient of inlet openings is provided. In one such embodiment this gradient increases from proximal to distal so that a clot that fails to enter a smaller more proximal opening may be trapped by a larger more distal opening as the device is retracted. In one such embodiment this gradient decreases from proximal to distal so that any clot entering a larger more proximal opening will not be able to exit a smaller more distal opening as the device is retracted. Such an outer member may be combined with a tapered inner member to further assist in clot demobilization and trapping—so that a clot entering through a large proximal opening of the outer member adjacent a small diameter portion of the inner member is prevented from migrating distally along the device by the increasing diameter of the more distal portion of the tapered inner member.

Various embodiments of the invention are described in more detail below. Within these descriptions various terms for each portion of the devices may be interchangeably used as discussed previously. Each of the described embodiments are followed by a list of further qualifications (preceded by the word "wherein") to describe even more detailed versions of the preceding headline embodiment. It is intended that any of these qualifications may be combined with any of the headline embodiments, but to maintain clarity and conciseness not all of the possible permutations have been listed.

In one embodiment of the invention the treatment apparatus comprises a clot retrieval device comprising:—an elongate member, and an expandable clot engaging element configured to extend across the clot in its expanded state, the expandable clot engaging element comprising a first monolithic structure and a second monolithic structure, the first monolithic structure encircling the second monolithic structure over at least a portion of its length, the second monolithic structure comprising a proximal section, an intermediate section and a distal section, the distal section comprising an expansion.

Some optional features of this embodiment include:
- wherein the first monolithic structure is configured to substantially encapsulate the second monolithic structure;
- wherein the first monolithic structure comprises a proximal section, an intermediate section and a distal section, the distal section comprising an enclosed distal end;
- wherein the distal end of the clot engaging element comprises an enclosed distal end said enclosed distal end configured to capture clot fragments and/or to prevent distal migration of clot fragments;
- wherein the expansion is configured to prevent clot fragment migration;
- wherein the distal end of the first monolithic structure comprises an enclosed distal end said enclosed distal end defining a surface the surface configured as a clot fragment barrier surface;
- wherein the clot fragment barrier surface comprises an interconnected network of struts;
- wherein the distal section of the clot engaging element is configured to provide a three dimensional barrier to clot migration;
- wherein the device further comprises an elongate connector element said elongate connector element comprising a proximal end and a distal end, the proximal end connected to the second monolithic structure and the distal end connected to the first monolithic structure;
- wherein the elongate connector element comprises a spring element and said spring element is integral with the second monolithic structure;
- wherein the first monolithic structure and the second monolithic structure are connected at their distal ends;
- wherein the first monolithic structure and the second monolithic structure are not connected at their distal ends; and/or
- wherein the proximal sections of said first and second monolithic structures are connected to a distal end of the elongate member.

In another embodiment of the invention the treatment apparatus comprises a clot retrieval device comprising:—an elongate member, and an expandable clot engaging element configured to extend across the clot in its expanded state, the expandable clot engagement element comprising a proximal segment, a clot engaging segment and a distal segment, the proximal segment configured to extend proximal of the clot in use and the distal end configured to extend distal of the clot in use, the clot engaging segment configured to engage with the clot in its expanded state, the distal end comprising a fragment protection structure, the fragment protection structure comprising a plurality of struts configured in a volumetric pattern.

Some optional features of this embodiment include: —
- wherein the volumetric pattern comprises at least partially a conically shaped volumetric pattern;
- wherein the volumetric pattern comprises at least partially a cylindrical volumetric pattern;
- wherein the volumetric pattern comprises at least one plurality of interconnected struts;
- wherein the volumetric pattern comprises at least two pluralities of interconnected struts;
- wherein the volumetric pattern comprises a first plurality of struts arranged about a first axis and a second plurality of struts arranged about a second axis;
- wherein the position of the first axis is moveable relative to the position of the second axis;
- wherein the first axis and the second axis comprise center lines and in use said center lines may comprise straight and/or curved center lines;
- wherein the centerlines are deflectable relative to one another; wherein the volumetric pattern comprises a terminal end;
- wherein the terminal end comprises a terminal junction for at least some of said plurality of struts;
- wherein the terminal end comprises a connection point at which said plurality of struts are terminated and/or connected;
- wherein the volumetric pattern comprises a first plurality of struts, and a second plurality of struts;
- wherein the second plurality of struts is at least partially encompassed by the first plurality of struts;
- wherein the second plurality of struts encircles the first plurality of struts;
- wherein the first plurality of struts is arranged about a first axis and the second plurality of struts is arranged about a second axis and said first and second axes are substantially parallel;
- wherein the first plurality of struts is arranged about a first axis and the second plurality of struts is arranged about a second axis and said first and second axes are substantially parallel;
- wherein the first plurality of struts comprises a conical shape; and or
- wherein the second plurality of struts comprises a spherical shape, a flattened spherical shape, a cylindrical shape or a spindle torus shape.

In another embodiment of the invention the treatment apparatus comprises a clot retrieval device comprising:—an elongate member, and an expandable clot engaging element comprising a first tubular structure and a second tubular structure, the first tubular structure at least partially encircling the second tubular structure, the first tubular structure comprising a proximal end, a distal end, a proximal termination and a distal termination, the second tubular structure comprising a proximal end, a distal end, a proximal termination and a distal termination, the proximal termination of the first and second tubular structures being connected to the elongate member and the distal terminations of the first and second tubular structures being connected to each other.

Some optional features of this embodiment include:
- wherein the first tubular structure and the second tubular structure comprise monolithic structures of interconnected struts;
- wherein the first tubular structure and the second tubular structure comprise longitudinally extending structures;

wherein both the first tubular structure and the second tubular structure comprise collapsed delivery configurations and expanded deployed configurations and the first tubular structure at least partially encircling the second tubular structure in both the expanded configurations and the collapsed configurations;

wherein one or both of the first tubular structure and the second tubular structure comprise a proximal collar for connecting one or both of the first tubular structure and the second tubular structure to a distal end of the elongate member;

wherein the at least one proximal collar comprises a partial collar; and/or wherein the at least one proximal collar is cut from a hypotube and encircles at least a portion of a distal end of the elongate member.

In another embodiment of the invention the treatment apparatus comprises a clot retrieval device comprising:—an elongate member, and an expandable clot engaging element comprising a first tubular structure and a second tubular structure, the first tubular structure at least partially encircling the second tubular structure, the first tubular structure and the second tubular structure connected to a distal end of the elongate member at a connection point, the first tubular structure comprising a first proximal connecting strut and a first connector element, the second tubular structure comprising a second proximal connecting strut and a second connector element, the first connector element encircling the second connector element at the connection point.

Some optional features of this embodiment include:
wherein the first connector comprises a collar;
wherein the second connector comprises a collar or partial collar; and/or
wherein the elongate member comprises a distal safety stop configured to prevent distal movement of the first connector and/or the second connector.

In another embodiment of the invention the treatment apparatus comprises a clot retrieval device comprising:—an elongate member, and an expandable clot engaging element configured to extend across the clot in its expanded state, the expandable clot engagement element comprising a first luminal structure and a second luminal structure, the first luminal structure being larger in diameter than said second luminal structure, the distal end of said first luminal structure comprising a plurality of struts converging towards the axis of the first luminal structure, the distal end of said second luminal structure comprising a plurality of struts diverging away from the axis of said second luminal structure.

Some optional features of this embodiment include:
wherein the distal end of said first and second luminal structures are configured to form a three dimensional clot fragment migration barrier;
wherein the distal end of said second luminal structure further comprises an inflection region where a tangent to said plurality of struts is substantially parallel to the axis of said second luminal structure;
wherein the distal end of said second luminal structure further comprises a converging region where said plurality of struts converged on the axis of said second luminal structure;
wherein the distal end of said second luminal structure further comprises a second distal junction where said plurality of struts terminate;
wherein the distal end of said first luminal structure further comprises a first distal junction where said plurality of struts terminate;

wherein the first distal junction is distal of the second distal junction; and/or
wherein the first distal junction is connected to the second distal junction by a connector element.

In another embodiment of the invention the treatment apparatus comprises a clot retrieval device comprising:—an elongate member, and a clot engaging element comprising a collapsed delivery state and an expanded clot engaging state, the clot engaging element configured to extend across the clot in its expanded state, the clot engaging element comprising a proximal section, an intermediate section and a distal section, the intermediate section comprising a luminal structure and the distal section comprising an expansion region.

Some optional features of this embodiment include:
wherein the diameter of the expansion region is larger than the diameter of the intermediate section in the expanded state;
wherein the clot engagement element comprising plurality of struts connected in a monolithic structure;
wherein the expansion region comprises a region of divergence and a region of convergence;
wherein the expansion region comprises an inflection point between the region of divergence and the region of convergence;
wherein the expansion region is integral with the intermediate section;
wherein the expansion region comprises a transition section the transition section comprising a plurality of struts connection the expansion region to the intermediate section;
wherein the expansion region comprises a tapering distal end;
wherein the device comprises an elongate member connected to the distal end of the expansion region; and/or
wherein in the expanded state the luminal structure is configured to define a flow lumen through the clot.

In another embodiment of the invention the treatment apparatus comprises a device for removing clot from a blood vessel comprising:—an elongate member, and an expandable clot engaging element configured to extend across the clot in its expanded state, the expandable clot engagement element comprising a first luminal structure and a second luminal structure, the first luminal structure being larger in diameter than said second luminal structure and encircling at least a portion of the second luminal structure, the second luminal structure comprising a clot capture structure at its distal end, the clot capture structure comprising a flared section.

Some optional features of this embodiment include:
wherein the clot capture structure comprises a plurality of struts and at least one fiber configured into a filter;
wherein in the expanded state the diameter of at least a portion of the clot capture structure is similar to the diameter of the blood vessel;
wherein in the expanded state the diameter of at least a portion of the clot capture structure is larger than the diameter of the second luminal structure; and/or
wherein in the expanded state the diameter of at least a portion of the clot capture structure is similar to the diameter of the first luminal structure.

In another embodiment of the invention the treatment apparatus comprises a clot retrieval device comprising an elongate member, a first expandable member and a second expandable member; both expandable members having a proximal section, a body section, and a distal section, the body section of the first expandable member in the freely expanded state being larger in diameter than that of the second expandable member in the freely expanded state, and the proximal section of the first expandable member being distal of the proximal section of the second expandable member.

Some optional features of this embodiment include:
wherein the distal section of the first expandable member comprises a clot capture structure;
wherein the distal section of the second expandable member comprises a clot capture structure;
wherein the clot capture structure comprises a plurality of struts;
wherein the clot capture structure comprises a plurality of struts and at least one fiber configured into a filter;
wherein the proximal end of the first expandable member is connected to the distal section of the elongate shaft;
wherein the proximal end of the first expandable member is connected to the second expandable member;
wherein the proximal end of the second expandable member is connected to the distal section of the elongate shaft;
wherein the distal end of the first expandable member is not connected to the distal end of the second expandable member;
wherein the distal end of the first expandable member is connected to the distal end of the second expandable member;
wherein the body section of the second expandable member in the freely expanded state is less than 50% of the diameter of the body section of the first expandable member in the freely expanded state;
wherein the body section of the second expandable member in the freely expanded state is less than 40% of the diameter of the body section of the first expandable member in the freely expanded state;
wherein the body section of the second expandable member in the freely expanded state is less than 30% of the diameter of the body section of the first expandable member in the freely expanded state; and/or
wherein the body section of the second expandable member in the freely expanded state is less than 20% of the diameter of the body section of the first expandable member in the freely expanded state.

A method of using a clot retrieval device to retrieve a clot from a vessel, said clot retrieval device comprising an expandable body and an elongate shaft, said method comprising: delivering the device through a microcatheter to a target site, retracting the microcatheter to deploy the device at least partially within or beneath the clot, expanding a proximal section of the expandable member within a proximal section of the clot to a diameter smaller than that of the vessel, expanding a distal section of the expandable member distal of the clot to a diameter substantially equal to that of the vessel, withdrawing the device and clot proximally and removing both from the patient.

Some optional features of this embodiment include:
wherein the expandable body comprises an inner expandable member and an outer expandable member;
wherein the expanded diameter of the inner expandable member is smaller than that of the outer expandable member;
wherein at least a portion of the inner expandable member extends within at least a portion of the outer expandable member;
wherein at least a portion of the inner expandable member extends proximal of the outer expandable member;
wherein the distal section of the expandable body comprises a clot capture structure;
wherein the clot capture structure is connected to the inner expandable member;
wherein the clot capture structure is connected to the outer expandable member; and/or
wherein the elongate shaft extends outside of the patient in use.

BRIEF DESCRIPTION OF THE DRAWINGS

The invention will be more clearly understood from the following description of some embodiments thereof, given by way of example only, with reference to the accompanying drawings, in which:

FIG. 1a shows a side view of a clot retrieval device of this invention;

FIG. 1b shows a side view of a clot retrieval device of this invention;

FIG. 1c shows a detail view of a portion of FIG. 1a;

DETAILED DESCRIPTION

Figure 2A:
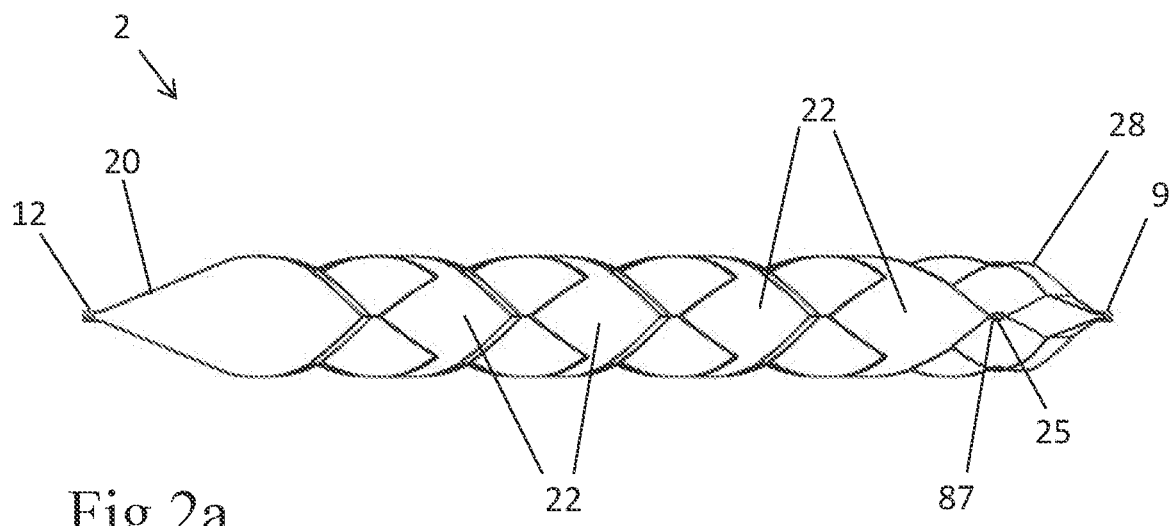
FIG. 2a shows a view of a component of a clot retrieval device of this invention.

Specific embodiments of the present invention are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in cath lab procedures. It is assumed in the descriptions below that these products and methods are employed in conjunction with the device and methods of this invention and do not need to be described in detail.

The following detailed description is merely exemplary in nature and is not intended to limit the invention or the application and uses of the invention. Although the description of the invention is in many cases in the context of treatment of intracranial arteries, the invention may also be used in other body passageways as previously described.

A common theme across many of the disclosed designs is a dual layer construction in which the device comprises an outer expandable member within which runs an inner expandable member, both members being directly or indirectly connected to an elongate shaft, and a distal net or scaffold configured at the distal end of the device to prevent the escape of clot fragments. This distal net may be appended to either the shaft, the inner or the outer members or to several of these. A range of designs are envisaged for each of these elements as described throughout this document, and it is intended that any of these elements could be used in conjunction with any other element, although to avoid repetition they are not shown in every possible combination.

Both the inner and outer expandable members are desirably made from a material capable of recovering its shape automatically once released from a highly strained delivery configuration. A superelastic material such as Nitinol or an alloy of similar properties is particularly suitable. The material could be in many forms such as wire or strip or sheet or tube. A particularly suitable manufacturing process is to laser cut a Nitinol tube and then heat set and electropolish the resultant structure to create a framework of struts and connecting elements. This framework can be any of a huge range of shapes as disclosed herein and may be rendered visible under fluoroscopy through the addition of alloying elements (such as Platinum for example) or through a variety of other coatings or marker bands.

The inner expandable member may in some cases form a generally tubular structure and is ideally configured to expand to a lesser diameter than that of the smallest vessel in which it is intended to be used. In the case of a generally non-tapered inner member this diameter is typically less than 50% that of the outer expandable member and may be as low as 20% or less of the outer member diameter.

FIGS. 1a and 1b show views from slightly different angles and orientations of one embodiment of a clot retrieval device of the present invention. The clot retrieval device 1 has an elongate shaft 6 having a distal end that extends interior of the artery and a proximal end that extends exterior of the artery, a clot engaging portion configured at the distal end of the elongate shaft 6 having an outer expandable member 2 comprising multiple expandable segments 26, and an inner expandable member 3 to facilitate restoration of blood flow through clot immediately after the clot retrieval device 1 is deployed at an obstructive site. The outer member 2 and inner expandable member 3 comprises a collapsed configuration for delivery and an expanded configuration for clot retrieval, flow restoration and fragmentation protection. In one embodiment the inner expandable member comprises a generally tubular body section. Outer member 2 comprises multiple inlet openings 22 through which clot can pass into an inner reception space 11 which is provided between the outer and inner expandable members. The outer expandable member 2 and the inner expandable member 3 are connected to the elongate shaft 6 at a proximal joint 12. The device also comprises a distal tip 8 which is appended to a distal joint 9 at the distal end of distal expandable segment 24. The distal portion of the inner expandable member is joined to that of the outer expandable member at distal joint 9.

The closed end of the distal expandable segment 28 prevents the egress of clot or clot fragments that have entered the reception space 11 between the inner and outer members. The expanded distal struts 10 of the inner member act as an additional three dimensional filter in combination with the closed distal end of the outer member 2 to further prevent the egress of clot or clot fragments. In certain embodiments this distal section may comprise fiber attachment points such as eyelets 87 or other fiber attachment features and fibers may be connected to the distal section at these attachment points to create a distal net.

The inner and outer members are preferably made of a super-elastic or pseudo-elastic material such as Nitinol or another such alloy with a high recoverable strain. Shaft 6 may be a tapered wire shaft, and may be made of stainless steel, MP35N, Nitinol or other material of a suitably high modulus and tensile strength. Shaft 6 has a coil 4 adjacent its distal end and proximal of the outer member 2 and inner expandable member 3. This coil 4 may be metallic and may be formed from stainless steel or from a more radiopaque material such as platinum or gold for example or an alloy of such a material. In another embodiment the coil 4 may be coated with a low friction material or have a polymeric jacket positioned on the outer surface of the coil.

FIG. 1c shows a close-up view of the area of the device highlighted by dashed ellipse 83 in FIG. 1a. Proximal radiopaque markers 82 are positioned at the distal end of struts 20 just proximal to two proximal crowns 81. This position is advantageous because it denotes the start of the fully expanded diameter of the device (as can be seen more clearly in FIG. 1b), which is the portion of the device that is most desirable to deploy under the clot for optimal grip of the clot. Thus these markers can be used to indicate to the physician where to deploy the device relative to the clot for an optimal result. Positioning these markers just proximal of crowns 81 provides greater space to make these markers as large (and thus visible) as possible. If positioned distal of crowns 81 the markers would be competing for space (when collapsed within a microcatheter) with struts 44 and 51 and would hence need to be made very small to avoid compromising the profile or deliverability of the device.

Figure 2B:
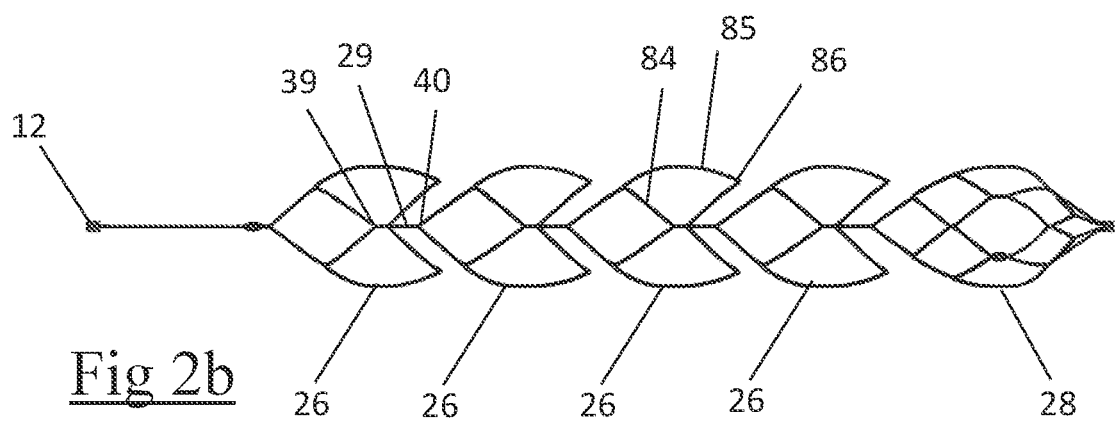
FIG. 2b shows a view of a component of a clot retrieval device of this invention.

FIG. 2a shows a plan view and FIG. 2b shows an elevation of the outer member 2. Outer member 2 comprises multiple expandable segments 26 interspersed with inlet openings 22 and terminating with a distal expandable basket segment 28. Proximal struts 20 are connected at their proximal ends to a collar 12 and at their distal ends to the first of expandable segments 26. The proximal struts 20 may have a tapered profile to ensure a gradual stiffness transition from the shaft 6 to the clot engagement section of the device. Each expandable segment 26 is connected to the segment distal to it by twin connecting arms 29, which run from proximal junctions 39 to distal junctions 40. In one embodiment these connecting arms comprise generally straight struts running parallel to the central axis of the device. In other embodiments these connecting arms may comprise a plurality of struts configured in one or more cells or may comprise curved or spiral arms. These connecting arms 29 thus act as hinge elements which allow the device to flex between expandable segments without compromising the ability of the segments to remain expanded and well apposed to the vessel wall. The region between each adjacent expandable segment comprises a pair of inlet mouths 22 through which clot may pass and enter the reception space 11 defined by the region between the inner and outer members. The inlet mouths 22 provide the added benefit of allowing the outer member 2 when retracted to apply a force to the clot in a direction substantially parallel to the direction in which the clot is to be pulled from the vessel (i.e. substantially parallel to the central axis of the vessel). This means that the outward radial force applied to the vasculature may be kept to a minimum, which in turn means that the action of the clot retrieval device 1 on the clot does not serve to increase the force required to dislodge the clot from the vessel, thus protecting delicate cerebral vessels from harmful radial and tensile forces. In one embodiment the connecting arms 29 between each expandable segment are substantially aligned with one another, while in another embodiment the connecting arms between a first pair of expandable segments may be positioned 90° to a second pair.

Each expandable segment 26 comprises a proximal ring of connected struts 84 and a plurality of distal "leaflets" 85. Each leaflet comprises a pair of struts terminating in a distal crown 86 to which no further elements are connected. The connected ring of struts 84 provides the segment with the radial force to open and expand when deployed under a clot. The leaflets 85 are able to deflect (like trapdoors) to allow clot to slide into the inlet openings 22. The combination of leaflets and hinge elements 29 allows the device to retain its expanded shape and remain in contact with the vessel wall as the device is retracted around bends and past branch vessels. During this retraction process the leaflets act to prevent clot from escaping from the device, closing the trapdoor and gently contacting the vessel wall.

One or more expandable members may comprise marker bands or radiopaque features such as gold or platinum marker or coils. In this embodiment three radiopaque markers 25 are shown fixed in eyelets 87 of the distal expandable member 28. The gold marker is positioned to indicate to the user the distal end of the barrel section of the outer member to aid in accuracy of deployment.

Figure 2C:
FIG. 2c shows a view of a component of a clot retrieval device of this invention in its unexpanded state.

FIG. 2c shows a developed view of the outer expandable member in its unexpanded state, such as when it is held within the lumen of a microcatheter for example. In one embodiment the outer expandable member is formed from a tube by laser cutting (or a similar material removal process) slots and removing material from the tube. In one embodiment this tube is of a very small diameter—much smaller than that of the expanded diameter of the outer expandable member, and ideally smaller than the inner lumen (diameter) of the microcatheter through which the device is designed to be delivered. Such a device would have a developed cut pattern similar to that of FIG. 2c in its unexpanded state. Cutting from such a small tube diameter creates significant manufacturing challenges but has significant advantages also in that it allows the distal end of the device to be easily formed into a conical "capture basket" shape and it allows proximal collar 12 to comprise a cylinder that will fit within the microcatheter lumen and can be very securely joined to elongate shaft 6.

Figure 2D:
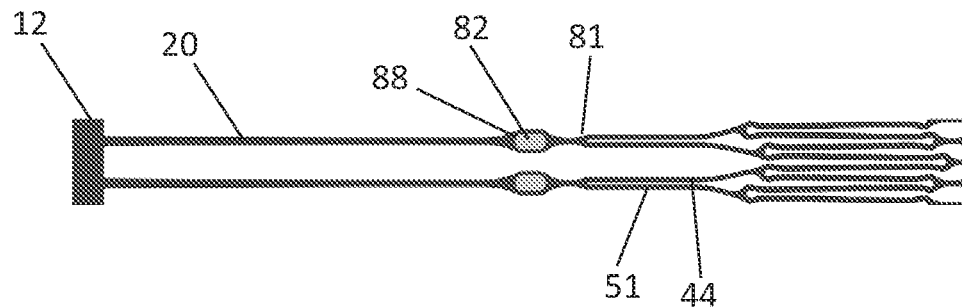
FIG. 2d shows a detail view of the proximal portion of FIG. 2c.

FIG. 2d shows a close up view of the proximal portion of the developed view shown in FIG. 2c. Proximal radiopaque markers 82 are located within eyelets 88 at the distal end of struts 20 just proximal to the two proximal crowns 81. This position is advantageous because it denotes the start of the fully expanded diameter of the device, which is the portion of the device that is most desirable to deploy under the clot for optimal grip of the clot. Thus these markers can be used to indicate to the physician where to deploy the device relative to the clot for an optimal result. Markers on other commercially available devices are generally positioned proximal, distal or within areas of the device that are intended to be deployed under the clot, and thus serve to indicate the location of the device without providing useful information to the user regarding optimal positioning of the device. The inventors have carried out extensive research into the ideal position to deploy such a device relative to the clot and have discovered that aligning the proximal edge of the "working length" of the device with the proximal face of the clot gives the best recanalization results. Hence these markers 82 are positioned at the proximal edge of this "working length", which is the length of the device that comprises clot scaffolding regions and clot inlet mouths and expands to the largest diameter when unconstrained.

Figure 3A:
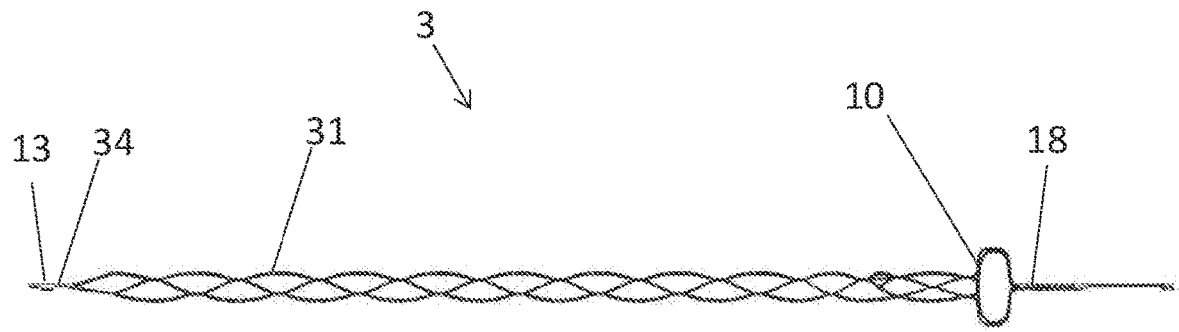
FIG. 3a shows a view of a component of a clot retrieval device of this invention.

FIG. 3a shows a side view of the inner expandable member 3. The inner expandable member 3 comprises a collapsed configuration for delivery and an expanded configuration for flow restoration and fragmentation protection. The inner expandable member 3 may comprise an elastic or super-elastic or shape-memory metallic structure and may further comprise a polished surface such as an electropolished surface. The inner expandable member 3 is configured so as to provide a flow lumen through the device 1 to facilitate the immediate restoration of blood flow past the clot upon deployment. In one embodiment the inner expandable member 3 is configured to scaffold said flow lumen through the clot to prevent the liberation of fragments which might otherwise lodge in the distal vasculature. Inner expandable member 3 comprises a generally cylindrical section of interconnected struts 31, which is connected at its proximal end by strut 34 to partial collar 13. The distal end of the inner expandable member 3 consists of an expansile section formed from expanded struts 10 which have a diameter greater than that of the body section of the inner expandable member 3. These expanded struts are connected to a coil section 18 which in this embodiment is laser cut from the tubing that the inner expandable member 3 is also cut from during processing. The distal end of the coil 18 on the inner expandable member 3 is bonded to the distal collar of the outer member 2 by adhesive.

The outer member 2 and the inner expandable member 3 are joined at the proximal and distal ends during assembly thereof to minimize tension within the members during use, the length of the outer member 2 should be substantially the same as the length of the inner expandable member 3 in the freely expanded configuration and the loaded configuration. The expanded struts 10 of the inner expandable member 3 elongate during loading so that the lengths of the inner and outer members are equal when fully loaded in a microcatheter. Length differentials between the inner expandable member 3 and the outer member 2 can still occur when the device is deployed in a small vessel or during the loading or deployment process. The coil 18 at the distal end of the inner expandable member 3 can accommodate minor length differentials by stretching without applying significant tensile or compressive forces to the device. In another embodiment this coil could be formed separately to the inner expandable member 3 and then be assembled to it. The coil could be formed from a stainless steel material, a polymer or from a more radiopaque metal such as gold or platinum or an alloy of such a material. The coil could also be replaced with a longitudinal length of an elastic material such as a low modulus polymer or elastomer.

Figure 3B:
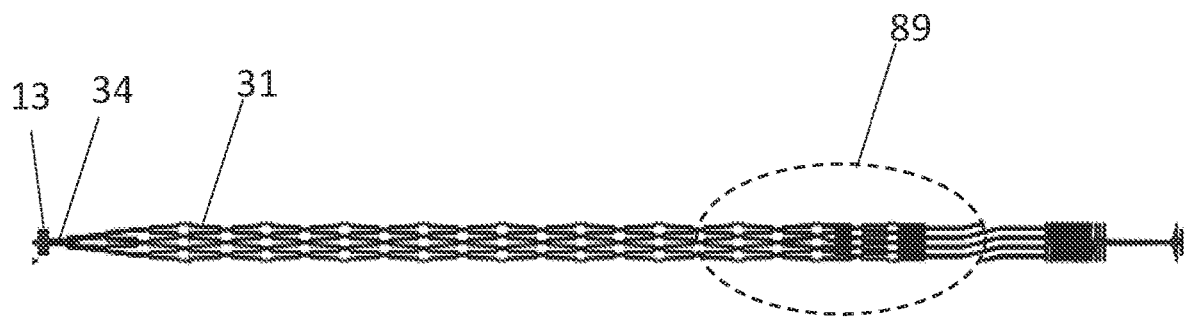
FIG. 3b shows a view of a component of a clot retrieval device of this invention in its unexpanded state.

FIG. 3b shows a developed view of the inner expandable member 3 in its unexpanded state, such as when it is held within the lumen of a microcatheter for example. In one embodiment the inner expandable member is formed from a tube by laser cutting (or a similar material removal process) slots and removing material from the tube. In one embodiment this tube is of a very small diameter—much smaller than that of its expanded diameter and ideally smaller than the inner lumen (diameter) of the microcatheter through which the device is designed to be delivered. Such a device would have a developed cut pattern similar to that of FIG. 3b in its unexpanded state.

Figure 3C:
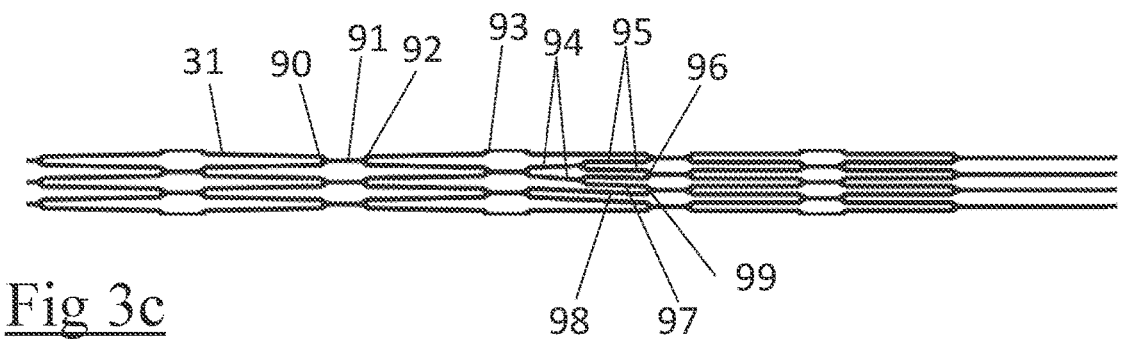
FIG. 3c shows a detail view of a portion of FIG. 2c.

FIG. 3c shows a detail view of the region of FIG. 3b highlighted by ellipse 89. In this close up view it can be seen that each cell of the inner member ends in a crown 90, to which is appended a connector element 91. Each of these connector elements then diverges at a first crown 92 into another pair of strut elements. One of each pair of these strut elements then converges with and is joined to one of an adjacent pair of strut elements at a second crown 93. This pattern is continued along the body of the member to maintain a constant number of cell elements around the circumference. In order to increase the number of cells around the circumference (to further reduce the porosity in a certain portion for example) a change in pattern is required. This is achieved by taking one pair of strut elements 94 and diverging each strut into a further pair of short strut elements 95. Thus four short strut elements 95 are created, and adjacent short strut elements converge and are connected at crown 96, while the other short strut elements 97 are connected to adjacent long struts 98 at crowns 99.

FIGS. 4a-4f shows a method of use of a device of this invention. A guidewire 103 and microcatheter 102 are inserted in the artery 100 and are advanced across the obstructive clot 101 using conventionally known techniques. When the microcatheter 102 is positioned distal to the occlusive clot 101, the guidewire 103 is removed from the artery 100 to allow the clot retrieval device 110 be advanced through the microcatheter 102. The device 110 is advanced in a collapsed configuration within the microcatheter 102 until the proximal radiopaque markers (not shown in FIG. 4c) of the device 110 align with the proximal margin 105 of the clot 101 under fluoroscopy.

Figure 4A:
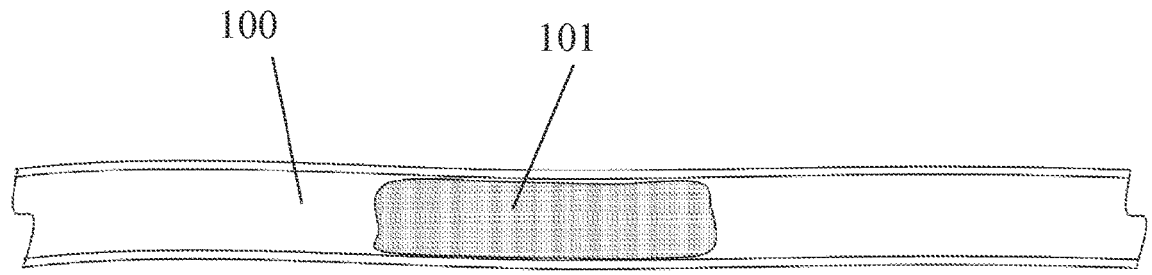
FIGS. 4a-4f illustrate a method of use of a device of this invention.
Figure 4B:
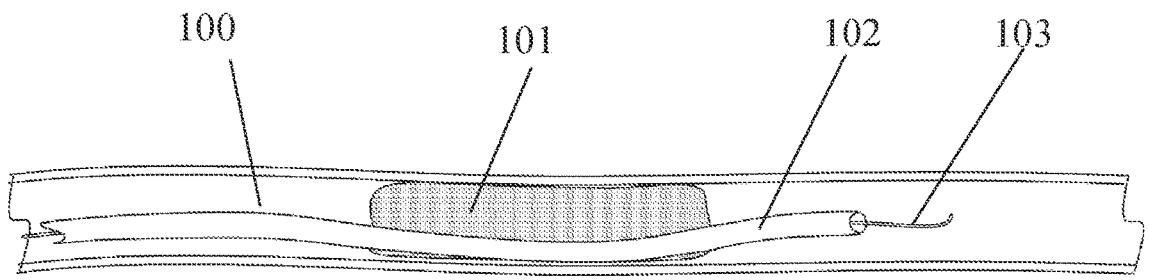
Figure 4C:
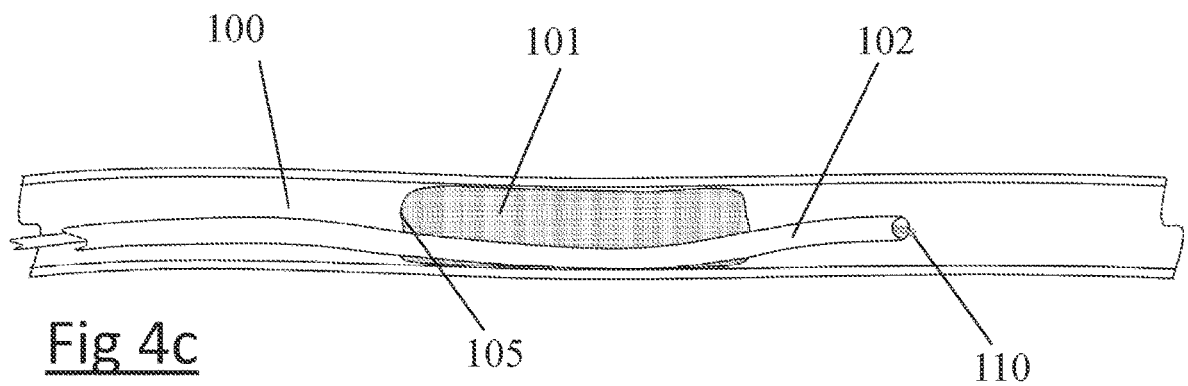
Figure 4D:
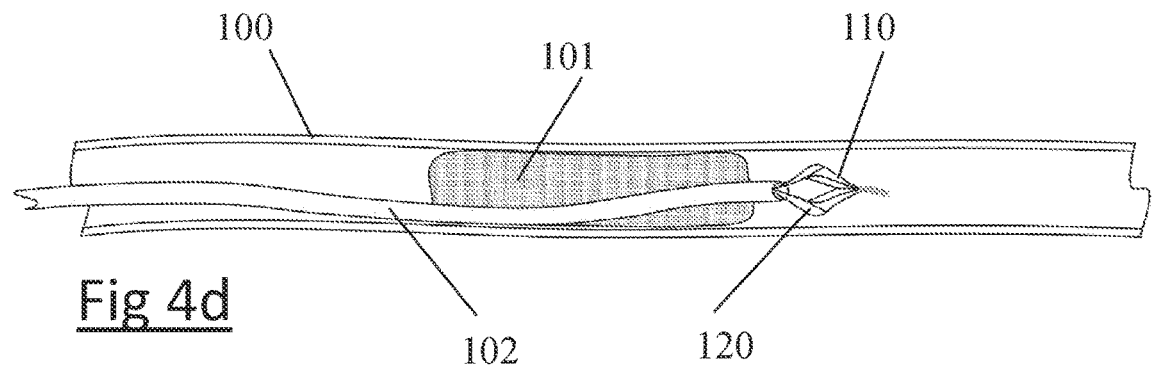
Figure 4E:
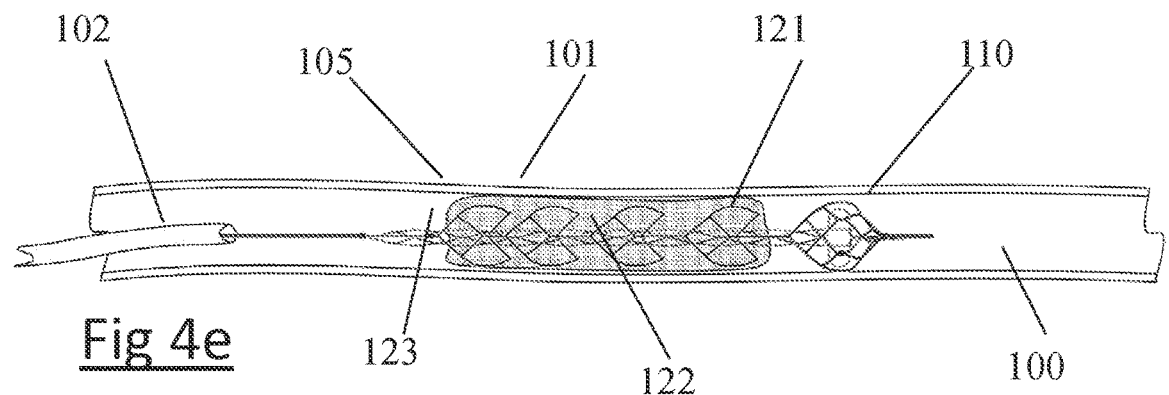

The microcatheter 102 is retracted while the position of device 110 is maintained static to deploy the clot retrieval device 110 across the clot 101. On deployment, the distal end 120 of the device 110 is preferably positioned distal of the clot 101. The device 110 expands so that the outer member 121 engages with the occlusive clot to facilitate clot retrieval from the vessel, and the inner tubular member 122 expands to provide a flow channel to restore blood flow in a controlled manner through the occlusive clot 101 to the vasculature distal of the occlusion. The inner channel 122 may also engage the clot 101 to provide additional grip for dislodgement. The device 110 may be allowed to incubate for a period of time within the clot 101 if desired, as controlled flow has been restored through the inner tubular member 122. FIG. 4e also shows the proximal radiopaque markers 123 aligned with the proximal margin 105 of the clot after device deployment from the microcatheter 102.

Figure 4F:
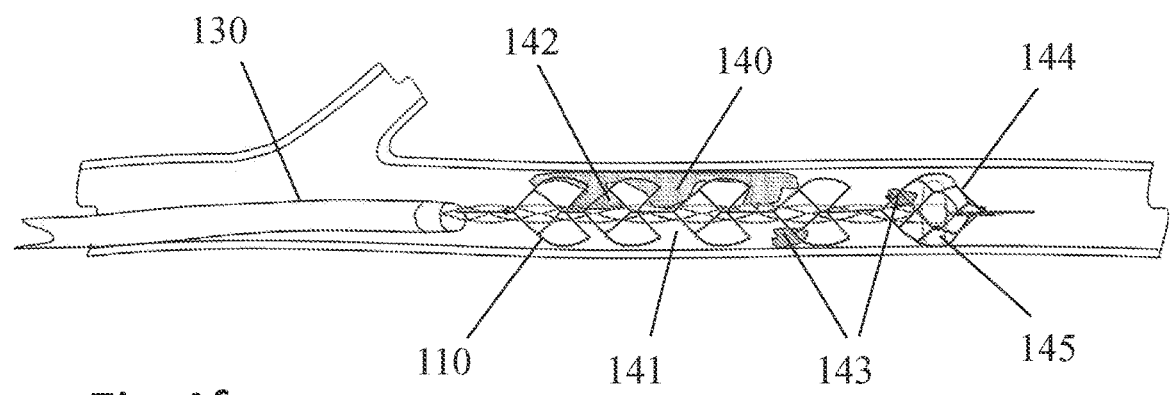

Retracting the device 110 dislodges the clot 101 from its position in the artery 100 and further withdrawal of the device retrieves the clot 101 until it can be retrieved into the guide catheter or introducer sheath 130. FIG. 4f illustrates the clot 140 engaged with the device 110 during retrieval into the guide catheter 130. The clot 140 is partially located in the inlet openings 141 of the device 110 and also partially located in the reception space 142 defined by the region between the inner and outer members. Clot fragments 143 are shown trapped in the distal end of the device 110 where the closed end of the outer member 144 and the expanded struts of the inner member 145 have prevented the fragments from being released in the blood flow. Flow occlusion, aspiration and other standard techniques may be used during the clot retrieval process. The device 110 may be rinsed in saline and gently cleaned before reloading in the insertion tool (not shown). The device 110 may be reintroduced into the microcatheter to be redeployed in additional segments of occlusive clot, if required.

Figure 5:
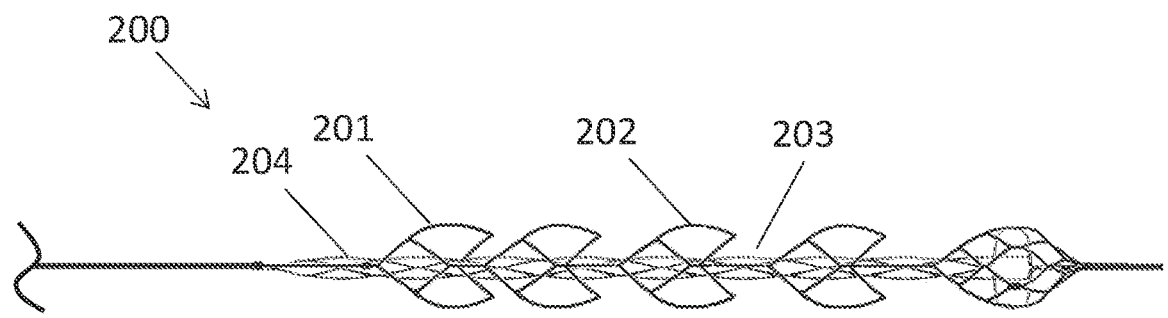
FIG. 5 shows a side view of a clot retrieval device of this invention.

FIG. 5 shows a side view of a clot retrieval device 200 of this invention similar in design and construction to device 1 of FIG. 1, but with a different outer member design. Outer member 201 comprises a series of expandable segments 202, separated by a series of inlet openings 203. In this embodiment the inlet openings increase in size along the length of the device, so that the proximal inlet opening is the smallest and the distal most one the largest. In other embodiments the inlet openings may be varied in size and position in other ways, such as alternating small/large or randomly sized. The device further comprises an inner expandable member 204, similar to other inner expandable members previously described herein.

Figure 6:
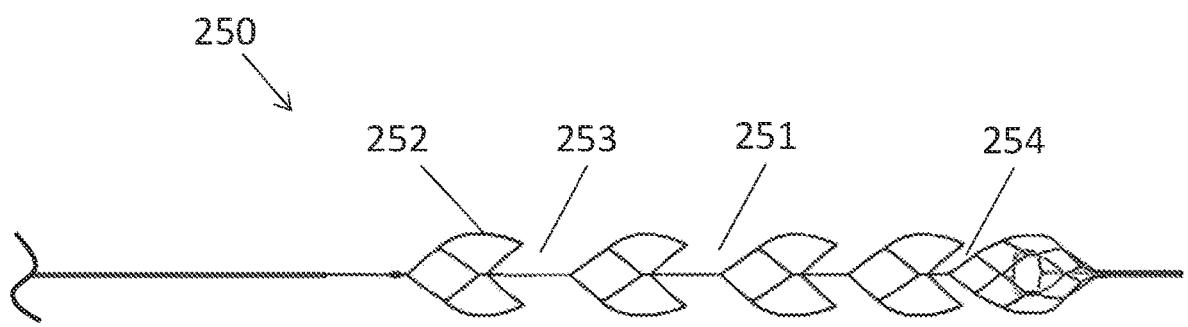
FIG. 6 shows a side view of a clot retrieval device of this invention.

FIG. 6 shows a side view of another clot retrieval device 250 of this invention similar to device 200 of FIG. 5, but without an inner expandable member. In this embodiment the inlet openings 251 of the outer member 252 decrease in size along the length of the device, so that the proximal inlet opening 253 is the largest and the distal most opening 254 the smallest. In other embodiments the inlet openings may be varied in size and position in other ways, such as alternating small/large or randomly sized.

Figure 7:
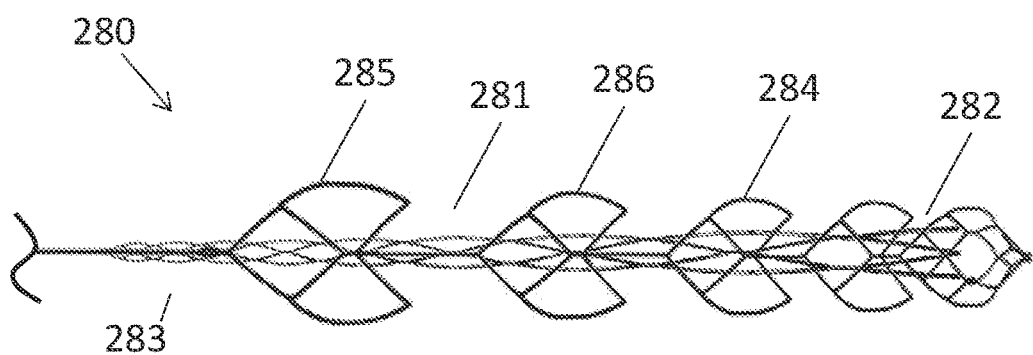
FIG. 7 shows a side view of a clot retrieval device of this invention.

FIG. 7 shows a side view of another clot retrieval device 280 of this invention similar to device 1 of FIG. 1. In this embodiment the inlet openings of the outer member decrease in size along the length of the device, so that the proximal inlet opening 281 is the largest and the distal most one 282 the smallest. The inner expandable member 283 is generally tubular and tapers from a small diameter proximally to a larger diameter distally. This combination of decreasing inlet opening size and increasing inner member diameter means that an embolus or clot entering a proximal inlet opening of the device is demobilized and prevented from migrating distally through the device and escaping from a more distal opening. In the embodiment shown the diameter of the outer member 284 is tapered in the opposite direction to that of the inner member, so that the proximal expandable segment 285 is larger in diameter than adjacent segment 286. This allows the device to conform well to the natural distal tapering of typical arterial vessels. In another embodiment the main body of the outer member may be generally constant in diameter. In yet another embodiment the main body of the outer member may taper in the opposite direction—with the distal most segment being largest in diameter so as to provide optimally protection against distal embolization as the device is retracted proximally into increasingly larger vessels.

It will be apparent from the foregoing description that, while particular embodiments of the present invention have been illustrated and described, various modifications can be made without departing from the spirit and scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

What is claimed is:

1. A clot retrieval device for removing occlusive clot from a blood vessel, the device comprising:
    an inner elongate body comprising a collapsed delivery configuration and an expanded deployed configuration; and
    an outer elongate body at least partially overlying the inner elongate body, the outer elongate body being expandable to a radial extent which is greater than the radial extent of the inner elongate body in the deployed configuration to define a clot reception space;

wherein the outer elongate body comprises a plurality of clot inlet openings and a plurality of clot engaging regions, wherein the clot engaging regions are adapted, on engagement with the occlusive clot, to urge the occlusive clot towards the clot inlet openings and into the clot reception space between the outer elongate body and the inner elongate body;

wherein a diameter of the inner elongate body varies along the length of the inner elongate body and a diameter of the outer elongate body varies along the length of the outer elongate body;

wherein the radial force profile of the device varies along the length of the device; and wherein a size of a first clot inlet opening of the plurality of clot inlet openings and a second clot inlet opening of the plurality of clot inlet openings is different than a size of the second clot inlet opening of the plurality of clot inlet openings and a third clot inlet opening of the plurality of clot inlet openings.

2. The device as claimed in claim 1 wherein the radial force at a distal end of the device is lower than that at a middle section of the device.

3. The device as claimed in claim 1 wherein and the radial force of one clot engaging region is different than the radial force of at least one other clot engaging region.

4. The device as claimed in claim 1 wherein the difference in radial force between the clot engaging regions is less than 20%.

5. The device as claimed in claim 1 wherein the outer elongate body comprises a diameter that tapers along the length of the device.

6. The device as claimed in claim 5 wherein the outer elongate body tapers from a smaller proximal diameter to a larger distal diameter.

7. The device as claimed in claim 5 wherein the outer elongate body tapers from a larger proximal diameter to a smaller distal diameter.

8. The device as claimed in claim 1 wherein in the expanded deployed configuration the inner elongate body expands to a diameter that is significantly smaller than a diameter of the blood vessel immediately adjacent to and distal of the occlusion.

9. The device as claimed in claim 1 wherein the inner elongate body comprises a diameter that varies between 0.75 mm and 2.5 mm.

10. The device as claimed in claim 1 wherein the inner elongate body comprises a diameter that varies between 0.75 mm and 1.75 mm.

11. The device as claimed in claim 1 wherein the inner elongate body comprises a generally conical shape.

12. The device as claimed in claim 1 wherein the inner elongate body comprises a diameter that tapers along the length of the device.

13. The device as claimed in claim 12, wherein the inner elongate body tapers from a smaller proximal diameter to a larger distal diameter.

14. The device as claimed in claim 12, wherein the inner elongate body tapers from a larger proximal diameter to a smaller distal diameter.

15. The device as claimed in claim 1 wherein the inner elongate body tapers from a diameter in a range of approximately 0.75 mm-1.75 mm to diameter in a range of approximately 1.5 mm-4.0 mm.

16. The device as claimed in claim 1 wherein there is a gradient of the size of the clot inlet openings in the outer elongate body along the length of the device.

17. The device as claimed in claim 16 wherein the gradient increases from proximal to distal.

18. The device as claimed in claim 16 wherein the gradient decreases from proximal to distal.

19. The device as claimed in claim 16 wherein the size of the inlet openings varies between approximately $1.0 \text{ mm}^2$ and approximately $3.0 \text{ mm}^2$.

20. A clot retrieval device for removing occlusive clot from a blood vessel, the device comprising:

an inner elongate body comprising a collapsed delivery configuration and an expanded deployed configuration; and an outer elongate body at least partially encircling the inner elongate body;

the outer elongate body being expandable to a radial extent which is greater than the radial extent of the inner elongate body in the deployed configuration to define a clot reception space;

the outer elongate body comprising a plurality of clot receiving openings and a plurality of clot engaging regions, wherein the clot engaging regions are adapted, on engagement with the occlusive clot, to urge the occlusive clot towards the clot receiving openings and into the clot reception space between the outer elongate body and the inner elongate body, wherein the outer elongate body comprises a framework formed by struts and crowns and wherein proximal radiopaque markers are located at a distal end of struts which are proximally adjacent to proximal crowns;

wherein a diameter of the inner elongate body varies along the length of the inner elongate body and a diameter of the outer elongate body varies along the length of the outer elongate body; and wherein a size of a first clot inlet opening of the plurality of clot inlet openings and a second clot inlet opening of the plurality of clot inlet openings is different than a size of the second clot inlet opening of the plurality of clot inlet openings and a third clot inlet opening of the plurality of clot inlet openings.

* * * * *